(12) United States Patent
Helgesson et al.

(10) Patent No.: US 6,510,847 B1
(45) Date of Patent: Jan. 28, 2003

(54) DELIVERY DEVICE

(75) Inventors: Per Helgesson, Lund (SE); Douglas Jennings, Herts (GB); Magnus Jeppsson, Lund (SE); Bruce Macmichael, Herts (GB); Michael Paton, Herts (GB)

(73) Assignee: AstraZeneca AB, Sodertalje (SE)

( * ) Notice: Subject to any disclaimer, the term of this patent is extended or adjusted under 35 U.S.C. 154(b) by 100 days.

(21) Appl. No.: 09/673,870

(22) PCT Filed: Jul. 7, 2000

(86) PCT No.: PCT/SE00/01470
§ 371 (c)(1), (2), (4) Date: Oct. 20, 2000

(87) PCT Pub. No.: WO01/03851
PCT Pub. Date: Jan. 18, 2001

(30) Foreign Application Priority Data

Jul. 12, 1999 (SE) ............................................. 9902672

(51) Int. Cl.[7] .............................................. A61M 11/00
(52) U.S. Cl. ......................... 128/200.23; 128/200.14; 128/203.12; 128/203.15; 128/203.18
(58) Field of Search ...................... 128/200.14, 200.23, 128/200.22, 203.12, 203.15, 207.18, 207.13, 206.18, 203.18; 239/338; 222/47, 168, 257, 380, 387, 383.3; 604/58, 94.01

(56) References Cited

U.S. PATENT DOCUMENTS

| | | | |
|---|---|---|---|
| 3,116,856 A | * | 1/1964 | Prussin et al. ......... 128/200.23 |
| 3,151,618 A | * | 10/1964 | Wakeman ............. 128/200.23 |
| 3,184,115 A | * | 5/1965 | Meshberg ............. 128/200.23 |
| 3,739,950 A | * | 6/1973 | Gorman ................. 128/200.23 |
| 3,789,843 A | * | 2/1974 | Armstrong et al. .... 128/200.23 |
| 4,114,811 A | * | 9/1978 | Loeffler ................. 128/200.23 |
| 4,509,515 A | * | 4/1985 | Altounyan et al. .... 128/200.23 |
| 4,678,106 A | * | 7/1987 | Newell et al. ......... 128/200.23 |
| 4,684,043 A | | 8/1987 | Foster et al. ................ 222/386 |
| 4,949,875 A | | 8/1990 | Kuo ........................... 222/156 |
| 5,119,806 A | * | 6/1992 | Palson et al. .......... 128/200.14 |
| 5,408,994 A | * | 4/1995 | Wass et al. ............ 128/200.14 |
| 5,465,873 A | | 11/1995 | Mejean et al. ................ 222/47 |
| 5,692,492 A | * | 12/1997 | Bruna et al. ........... 128/200.14 |
| 6,273,084 B1 | * | 8/2001 | Frid ....................... 128/200.14 |

FOREIGN PATENT DOCUMENTS

| | | | | |
|---|---|---|---|---|
| DE | 3544985 | 6/1987 | | 47/34 |
| EP | 0114617 | 1/1984 | | |
| EP | 0 804 935 | 11/1997 | | |
| FR | 686 891 | 7/1930 | | 20/3 |
| WO | WO 92/20455 | 11/1992 | | |

OTHER PUBLICATIONS

JP 7242278, Abstract.
International Search Report PCT/SE 00/01470.

* cited by examiner

Primary Examiner—Glenn K. Dawson
Assistant Examiner—Darwin P Erezo
(74) Attorney, Agent, or Firm—Fish & Richardson P.C.

(57) ABSTRACT

A manually-actuated device for the deliver of a volume of liquid which includes an outlet through which liquid is in use delivered and a cover member which is movably disposed relative to the housing between a first position in which the cover member at least partly covers the outlet and a second position in which the cover member acts as a lever which in use is acted upon by a user to actuate the delivery device.

25 Claims, 11 Drawing Sheets

DELIVERY DEVICE

BACKGROUND OF INVENTION

The present invention relates to a manually-actuated delivery device for the delivery of a volume of liquid, in particular a liquid containing medicament.

WO-92/20455 discloses one example of such a delivery device which takes the form of a nasal inhaler for the delivery of a volume of liquid containing medicament as a spray into a nasal cavity. This delivery device includes a nosepiece, in the form of an elongate tubular section, for insertion into one of the nasal cavities, through the distal end of which the spray is delivered, and is configured to be manually actuated on the application of a force axially relative to the longitudinal axis of the nosepiece.

Whilst such a delivery device is capable of delivering a metered volume of liquid, the use of that delivery device as a nasal inhaler can prove troublesome as the axial application of the manual actuation force tends to cause axial movement of the nosepiece within the nasal cavity which leads to inefficient delivery of the liquid.

BRIEF SUMMARY OF THE INVENTION

It is an aim of the present invention to provide an improved manually-actuated delivery device where the force for manual actuation is applied substantially orthogonally to the axis of the delivered liquid. With this configuration, when the delivery device is embodied as a nasal inhaler, the problem of the nosepiece being inadvertently withdrawn from the nasal cavity is obviated.

It is a further aim of the present invention to provide a delivery device which prevents further actuation after a predetermined number of actuations. In this way, a user is prevented from using the delivery device when empty.

Accordingly, the present invention provides a manually-actuated delivery device for the delivery of a volume of liquid, comprising:
  a housing which includes an outlet (27) through which liquid is in use delivered; and
  a cover member (39) which is movably disposed relative to the housing between a first position in which the cover member (39) at least partly covers the outlet (27) and a second position in which the cover member (39) acts as a lever which in use is acted upon by a user to actuate the delivery device, characterised in that the force applied by the user to the lever is substantially orthogonal to the axis of the delivered liquid.

Preferably, the cover member is, in the first position thereof, configured completely to cover the outlet.

Preferably, the cover member is rotatably mounted to the housing.

Preferably, the delivery device further comprises a liquid delivery assembly which includes a liquid delivery unit which is configured to be actuated to deliver a volume of liquid to the outlet on actuation of the delivery device.

More preferably, the liquid delivery unit comprises a container for containing liquid and a pump for delivering a volume of liquid from the container to the outlet.

Still more preferably, the pump comprises a body and a tubular element which is movable relative to the body and through which a volume of liquid is in use delivered on movement thereof relative to the body.

Preferably, the delivery device further comprises a coupling member which is movably disposed to the housing and configured to be engaged by the cover member in the second position thereof and cause actuation of the liquid delivery unit when the cover member is acted upon by the user.

More preferably, the liquid delivery assembly is movably disposed to the housing such as to cause actuation of the liquid delivery unit when moved between first and second positions and the coupling member is configured to move the liquid delivery assembly between the first and second positions when the cover member is acted upon by the user.

Still more preferably, the liquid delivery assembly includes at least one projection and the coupling member includes at least one arm which is configured in use to engage the at least one projection to move the liquid delivery assembly between the first and second positions.

Yet more preferably, the liquid delivery assembly is slideably disposed to the housing.

Preferably, the coupling member is rotatably mounted to the housing.

More preferably, the axes of rotation of the cover member and the coupling member are parallel.

Still more preferably, the axes of rotation of the cover member and the coupling member are co-axial.

Preferably, the liquid delivery assembly further includes a carrier unit to which the liquid delivery unit is attached.

Preferably, the liquid delivery unit includes a component which is moved on actuation thereof; and an indicator for providing an indication as to the number of actuations of the delivery unit, which indicator includes a rotatable member which is configured to be rotated by actuation of the delivery unit; wherein the rotatable member includes one of a resiliently-biased element or a locking surface and the component includes the other of the resiliently-biased element or locking surface, which resiliently-biased element and locking surface are configured such that the component is locked in position so as to prevent further actuation of the delivery unit once the delivery unit has been actuated a predeterminable number of times.

In one embodiment the rotatable member is configured to be rotated on each actuation of the delivery unit.

Preferably, the component is configured so as to move substantially parallel to the axis of rotation of the rotatable member.

Preferably, the component is reciprocally movable.

Preferably, the rotatable member includes the resiliently-biased element and the component includes the locking surface.

Preferably, the locking surface is provided by an opening.

More preferably, the opening is a through opening.

Preferably, the rotatable member is disposed about the component.

More preferably, the rotatable member is disposed about an outer surface of the component.

Still more preferably, the outer surface of the component is cylindrical and the rotatable member is circular.

The present invention also extends to inhalation devices incorporating the above-described delivery devices.

BRIEF DESCRIPTION OF THE DRAWINGS

A preferred embodiment of the present invention will now be described hereinbelow by way of example only with reference to the accompanying drawings, in which.

DETAILED DESCRIPTION OF THE INVENTION

Figure 1:
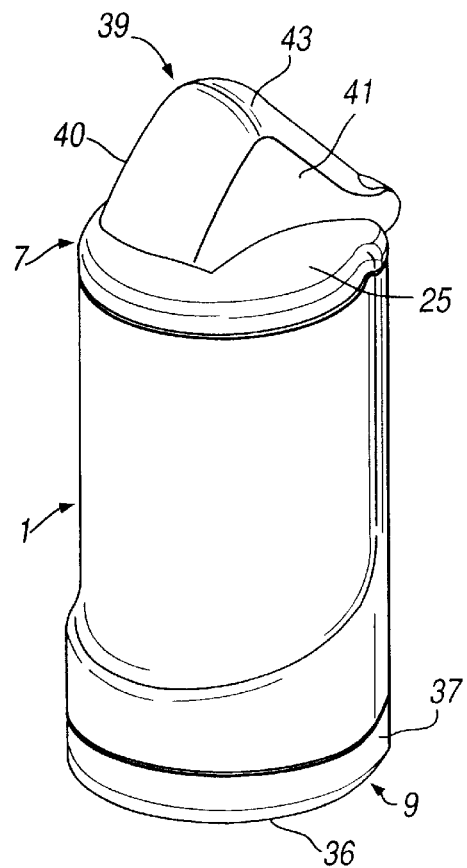
FIGS. 1 and 2 illustrate respectively front and rear perspective views of a delivery device in accordance with a preferred embodiment of the present invention.
Figure 2:
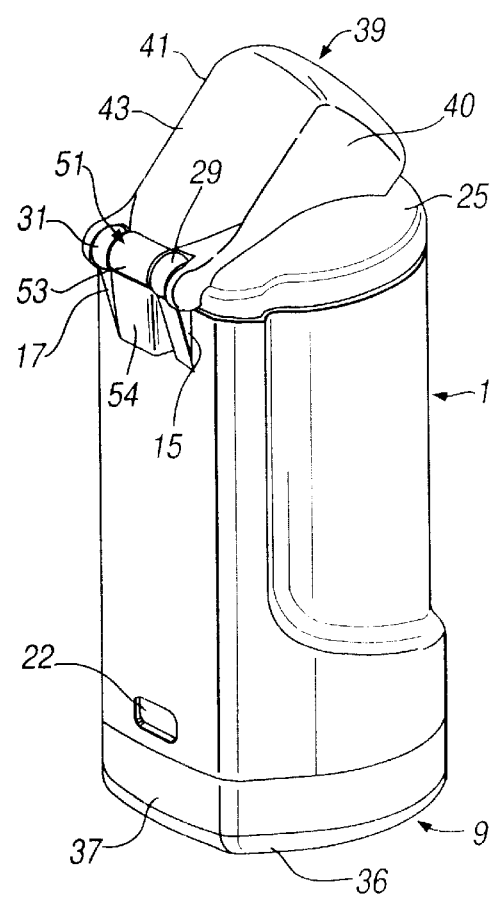
Figure 3:
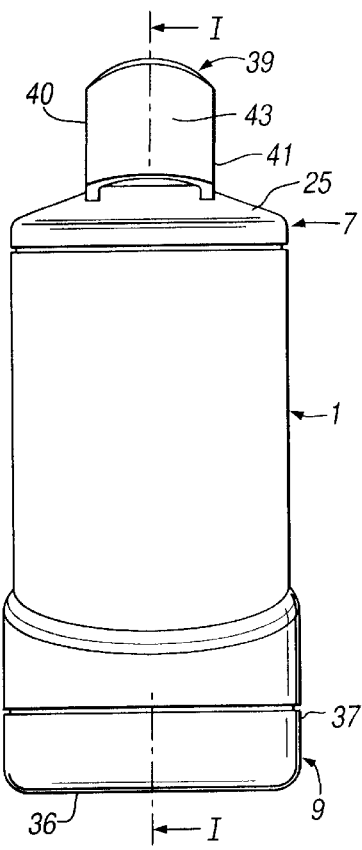
FIGS. 3 to 5 illustrate side views of the delivery device.
Figure 4:
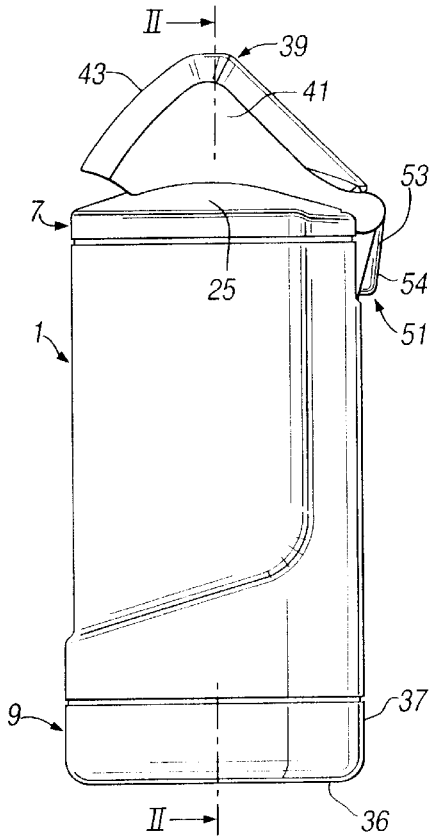
Figure 5:
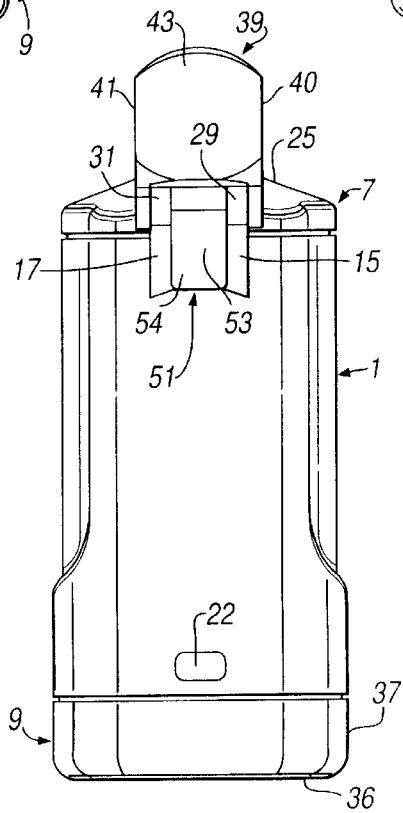
Figure 6:
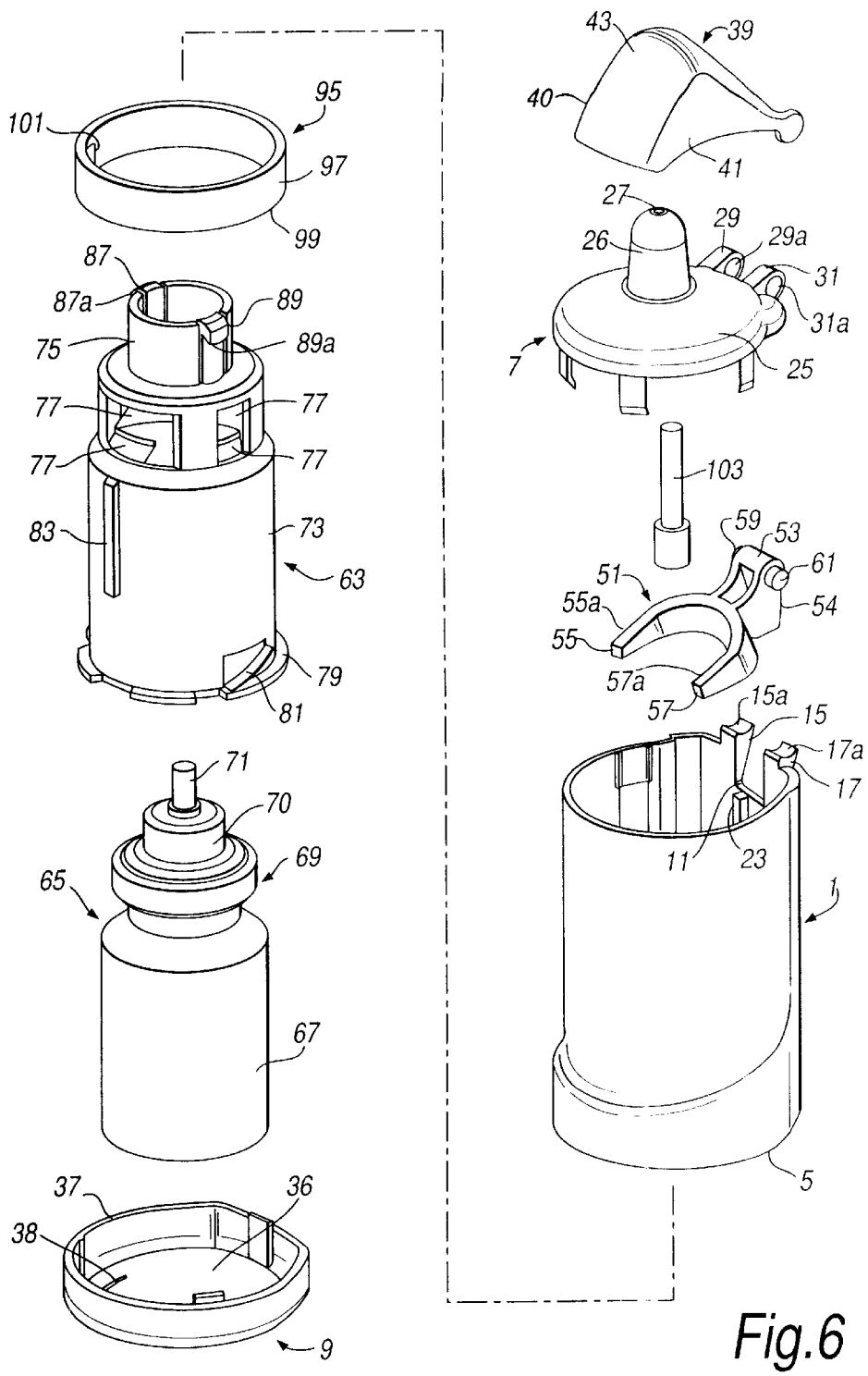
FIG. 6 illustrates an exploded front perspective view of the delivery device.
Figure 7:
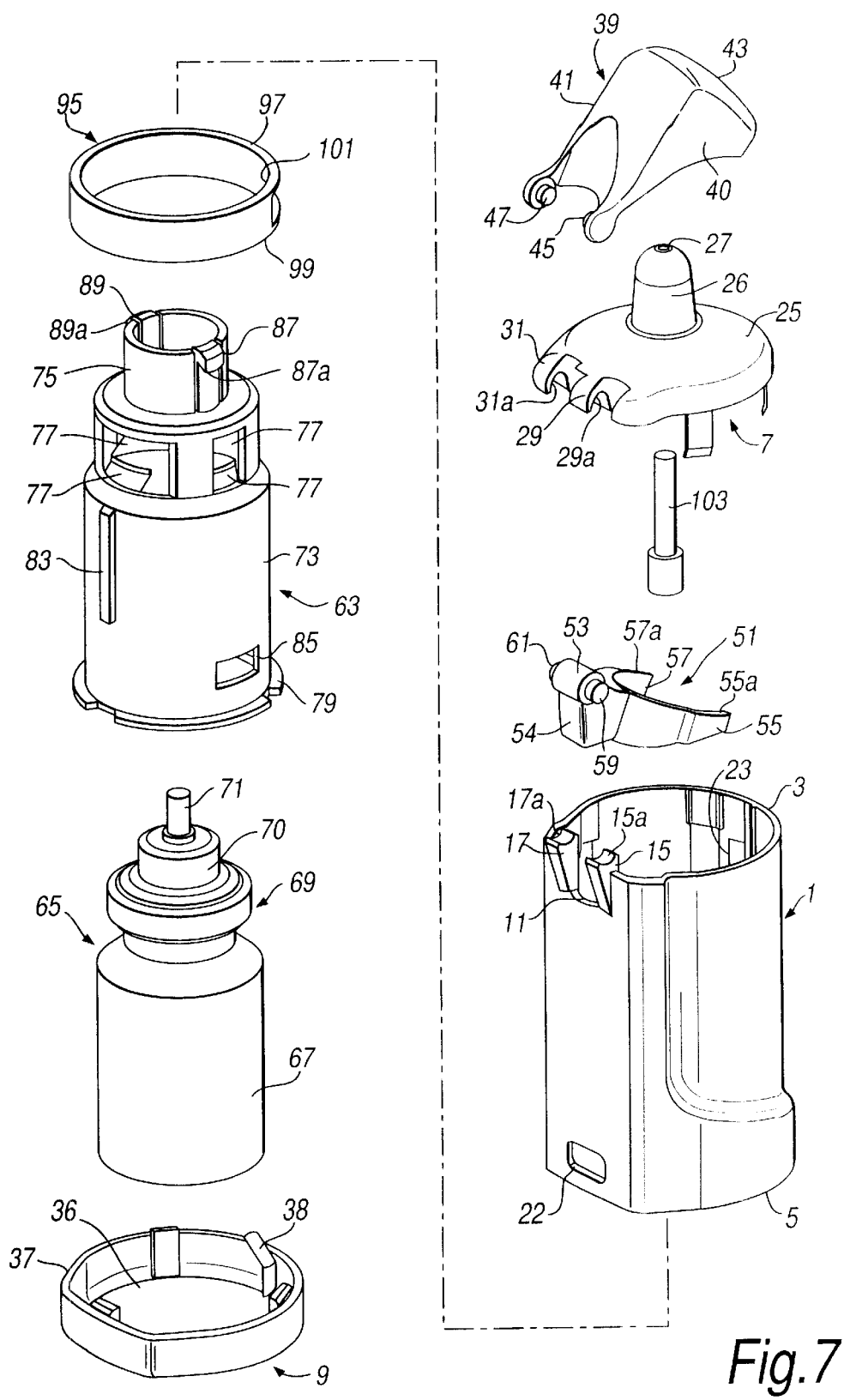
FIG. 7 illustrates an exploded rear perspective view of the delivery device.
Figure 8:
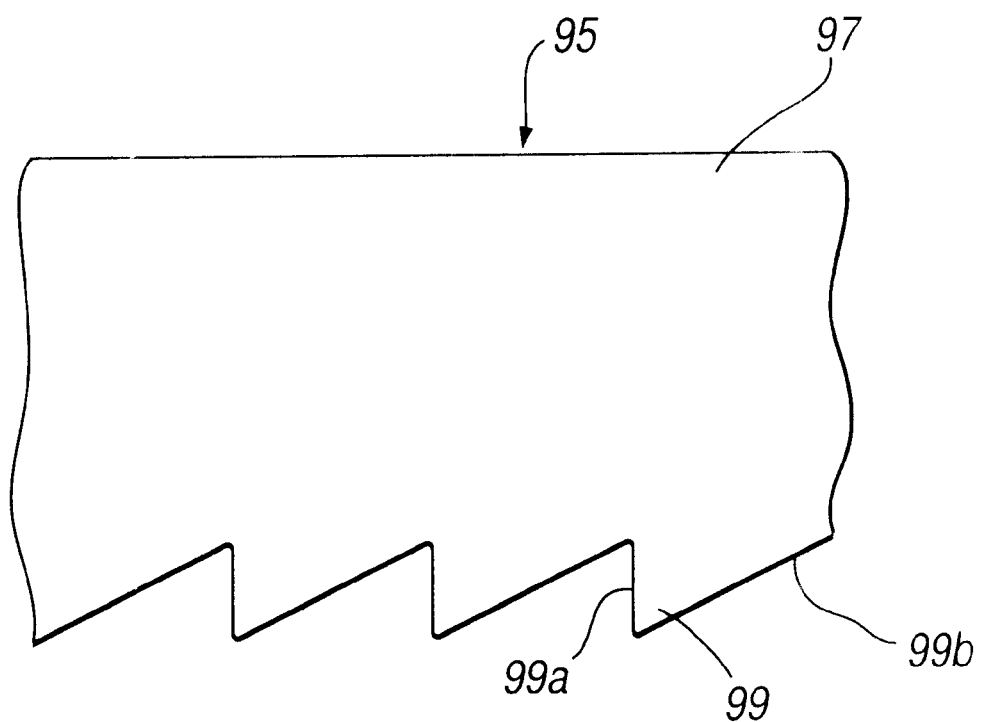
FIG. 8 illustrates in enlarged scale a fragmentary side view of the dose indicator of the delivery device.

The delivery device comprises a main body part 1, in this embodiment a generally cylindrical tubular section, which includes first and second open ends 3, 5, and first and second end body parts 7, 9 which are attached to the main body part 1 so as to enclose the open ends 3, 5 thereof and define an enclosed housing. In this embodiment the main body part 1 and the first and second end body parts 7, 9 are formed of a plastics material and joined by a plastics weld, for example, as achieved by ultrasonic welding.

The main body part 1 includes a first lateral opening 11, in this embodiment of substantially square shape, at the first end 3, one side of which first lateral opening 11 is open at the first end 3 and the adjacent sides of which extend substantially parallel to the longitudinal axis of the main body part 1. The main body part 1 further includes first and second lugs 15, 17 which are located at respective ones of the longitudinally-extending sides of the first lateral opening 11 and extend outwardly and upwardly of the first end 3. Each of the first and second lugs 15, 17 includes a part-cylindrical bearing surface 15a, 17a for hingeably supporting a yoke member 51 as will be described further hereinbelow. The main body part 1 still further includes a second lateral opening 22 adjacent the second end 5 which acts as a window for viewing a dose indicator 95 as will be described further hereinbelow. The main body part 1 yet further includes on the inner surface thereof a plurality of longitudinally-extending elongate slots 23 for receiving correspondingly-configured ribs 83 on a carrier unit 63 disposed therewithin as will be described further hereinbelow. The main body part 1 yet still further includes on the inner surface thereof a radially-directed flange 24 which acts as an abutment for the upper edge of a ring element 97 of the dose indicator 95.

The first body part 7 comprises a substantially planar wall member 25 which is of the same dimension as the first end 3 of the main body part 1 so as to close the same when attached thereto and a tubular section 26 which extends outwardly from the plane of the wall member 25 so as to provide a nosepiece and includes a spray orifice and outlet 27 at the distal end thereof through which a spray of liquid is in use ejected. In this embodiment the tubular section 26 is slightly inwardly tapered away from the wall member 25 and includes a rounded distal end so as to provide for ease of insertion into a nasal cavity and comfort of fit when so inserted. The first end body part 7 further includes first and second lugs 29, 31 which extend outwardly from the periphery of the wall member 25 in such a configuration as to mate with the respective ones of the first and second lugs 15, 17 on the main body part 1. Each of the first and second lugs 29, 31 includes a part-bearing surface 29a, 31a in this embodiment part-cylindrical in section, which part-bearing surfaces 29a, 31a together with the respective part-bearing surfaces 15a, 17a provided by the lugs 15, 17 on the main body part 1 define first and second bearings which provide a hinge axis.

The second end body part 9 comprises a substantially planar wall member 36 which is of the same dimension as the second end 5 of the main body part 1 and an upwardly-directed flange 37 which extends around the periphery of the wall member 36 by which the second end body part 9 is attached to the second end 5 of the main body part 1 so as to close the same. The second end body part 9 further includes a resilient element 38 which is disposed adjacent the inner surface of the upwardly-directed flange 37 thereof and extends upwardly and forwardly from the upper, inner surface of the wall member 36 thereof in one sense, in this embodiment in the counter-clockwise sense when viewed from above.

The delivery device further comprises a cover member 39 for covering the tubular section 26 which provides the nosepiece. The cover member 39 comprises first and second side wall members 40, 41, in this embodiment of generally triangular shape, which are configured to be disposed adjacent opposed sides of the tubular section 26 in the closed position of the cover member 39, and an interconnecting wall member 43 which interconnects the first and second side wall members 40, 41. The side wall members 40, 41 each include an opposed projection 45, 47 on the inwardly-directed surface thereof about which the cover member 39 is hingeable. The opposed projections 45, 47 are disposed such as to be located in the first and second bearings provided by the part-bearing surfaces 15a, 17a defined by the lugs 15, 17 on the main body part 1 and the part-bearing surfaces 29a, 31a defined by the lugs 29, 31 on the first end body part 7.

The delivery device further comprises a yoke member 51 which is pivotally mounted relative to the main body part 1. The yoke member 51 comprises a body part 53 which extends through the first lateral opening 11 in the main body part 1 and includes a surface 54 at the first lateral opening 11 which acts as a bearing surface and first and second laterally-spaced arms 55, 57 which are disposed in the main body part 1 and each include a bearing surface 55a, 57a at an upper surface thereof. The body part 53 further includes first and second oppositely-directed projections 59, 61 which are disposed such as to be located respectively in the first and second bearings provided by the part-bearing surfaces 15a, 17a defined by the lugs 15, 17 on the main body part 1 and the part-bearing surfaces 29a, 31a defined by the lugs 29, 31 on the first end body part 7.

The delivery device yet further comprises a carrier unit 63 which is slideably disposed in the main body part 1 and a liquid dispensing unit 65 which is attached to the carrier unit 63 such as to be slideably disposed concomitantly therewith.

The liquid dispensing unit 65 comprises a container 67, in this embodiment a bottle, which defines a chamber containing liquid, in this embodiment a liquid containing medicament, and a manually-actuated pump 69 which is attached, for example, by crimping, to the container 67 and when actuated delivers a metered volume of liquid. The pump 69 comprises a body 70 and a tubular delivery element 71 which extends from the body 70 and through which a metered volume of liquid is ejected when depressed into the body 70.

The carrier unit 63 comprises a first tubular section 73 in which the container 67 and a major part of the body 70 of the pump 69 is located and a second tubular section 75 connected to one, the upper, end of the first tubular section 73 through which extends the tubular delivery element 71 of the pump 69.

The first tubular section 73 includes a plurality of inwardly-directed resilient projections 77 which are configured to engage the body 70 of the pump 69 and lock the liquid delivery unit 65 in position in relation to the carrier unit 63. The first tubular section 73 further includes an outwardly-directed radial flange 79 at the other, lower, end thereof and a resilient element 81 which extends upwardly and forwardly from the upper surface of the flange 79 in the one sense, that is, the counter-clockwise sense when viewed from above. The first tubular section 73 still further includes a plurality of ribs 83 on the outer surface thereof which are located in the respective slots 23 at the inner surface of the main body part 1 and act to guide the travel of the carrier unit 63 in the main body part 1 and prevent relative rotation of the same. The first tubular section 73 yet further includes a lateral opening 85 adjacent the other, lower end thereof.

The second tubular section 75 includes first and second oppositely-directed projections 87, 89 at one, the upper, end thereof. Each of the first and second projections 87, 89 includes a part-cylindrical bearing surface 87a, 89a at the lower surface thereof which in use is engaged by the respective bearing surfaces 55a, 57a on the first and second arms 55, 57 of the yoke member 51.

The delivery device yet further comprises a dose indicator 95 for providing an indication as to the usage of the delivery device. In this embodiment the dose indicator 95 comprises a ring element 97 of rectangular section which is located about the outer surface of the first tubular section 73 of the carrier unit 63 such that the upper edge thereof abuts the radially-directed flange 24 on the inner surface of the main body part 1 and is configured such as to be rotatable thereabout in the one sense, that is, the counter-clockwise sense when viewed from above. With this configuration, a part of the outer surface of the ring element 97 is visible through the second lateral opening 22 in the main body part 1. In this embodiment the outer surface of the ring element 97 includes numerals of decreasing value for indicating the number of times the delivery device may still be actuated. In another embodiment the outer surface of the ring element 97 could be provided with numerals of increasing value for indicating the number of times the delivery device has already been actuated. Alternatively, or additionally, the ring element 97 may have a circumferential band of changing width along its length, such that the width visible is representative of the number of doses delivered or remaining. Colour changes may also be used to indicate the number of doses delivered or remaining. Such colour changes may also be applied in conjunction with the indications described hereinabove. For instance, by using numerals of different colour, or, by using a band, the colour of which changes along its length. The dose indicator 95 includes a plurality of teeth 99 disposed about the lower edge of the ring element 97 by which the dose indicator 95 is rotated about the first tubular section 73 of the carrier unit 63 through engagement with the distal end of the resilient element 81 on the carrier unit 63 on actuation of the delivery device. Each of the teeth 99 includes a first, driving surface 99a which faces in the other sense, that is, the counter-clockwise sense when viewed from below, and a second, guiding surface 99b which includes a component which faces in the one, opposite, clockwise sense. The dose indicator 95 further includes a resilient element 101 which extends inwardly and forwardly from the ring element 97 in the sense of rotation thereof, that is, the one, counter-clockwise sense when viewed from above. The resilient element 101 is configured normally to contact the outer surface of the first tubular section 73 of the carrier unit 63, but, as will be described further hereinbelow, to locate in the lateral opening 85 in the first tubular section 73 of the carrier unit 63 when the delivery device has been actuated a predetermined number of times so as to lock the carrier unit 63 in a fixed position and thereby prevent further use of the delivery device when the accuracy of the metered dose could not be ensured because of the small volume of liquid remaining in the container 67 of the liquid delivery unit 65.

The delivery device yet still further comprises a tubular feed element 103 which is attached to the tubular delivery element 71 of the pump 69 and disposed in the tubular section 26 of the first end body part 7 so as to provide a communication path between the pump 69 and the spray orifice 27 in the tubular section 26 through which a spray of a metered volume of liquid is ejected on each actuation of the delivery device.

Figure 9:
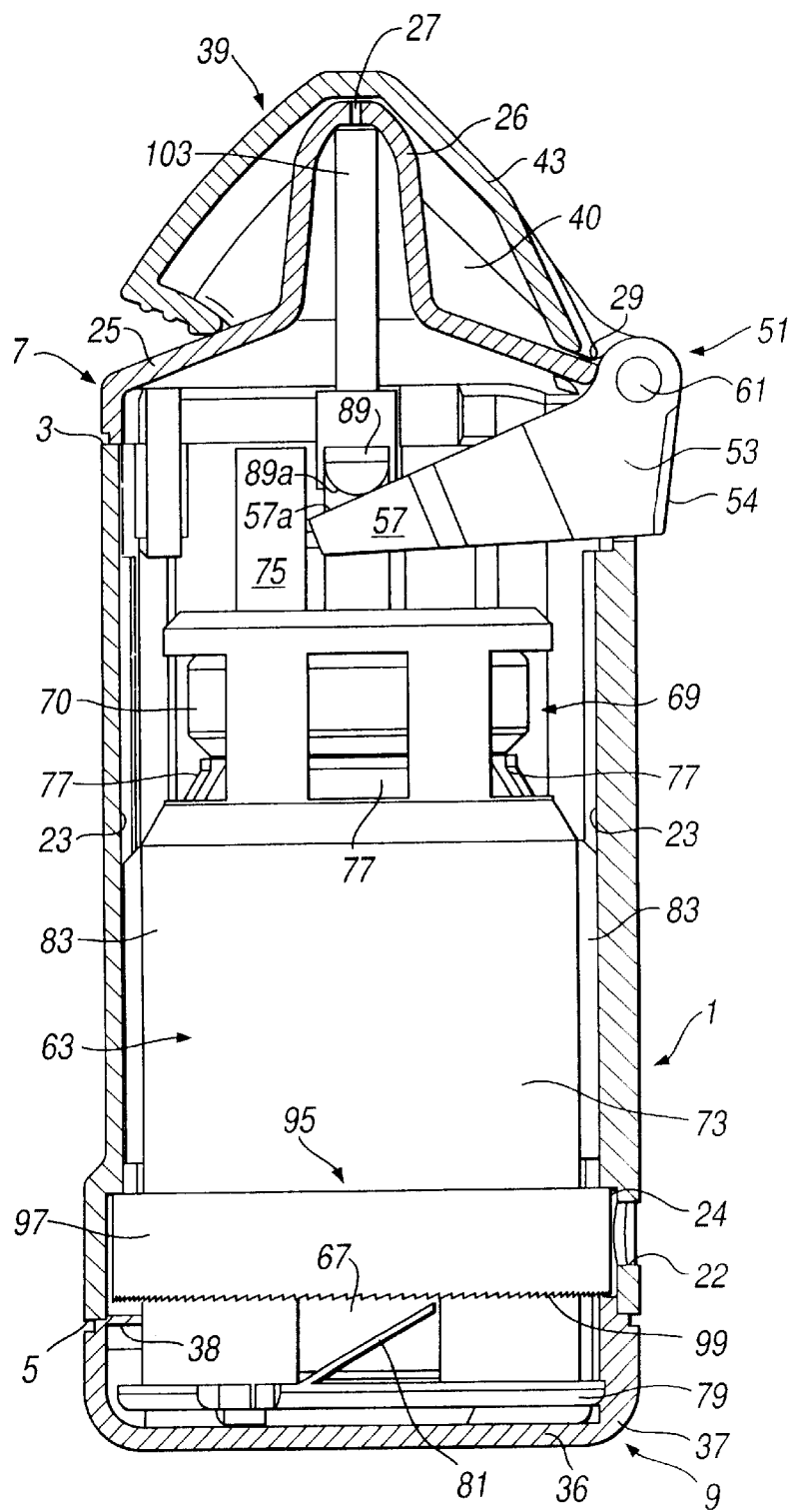
FIGS. 9 and 10 illustrate vertical sectional views (along sections I—I and II—II in FIGS. 3 and 4 respectively) of the delivery device in the closed configuration.
Figure 10:
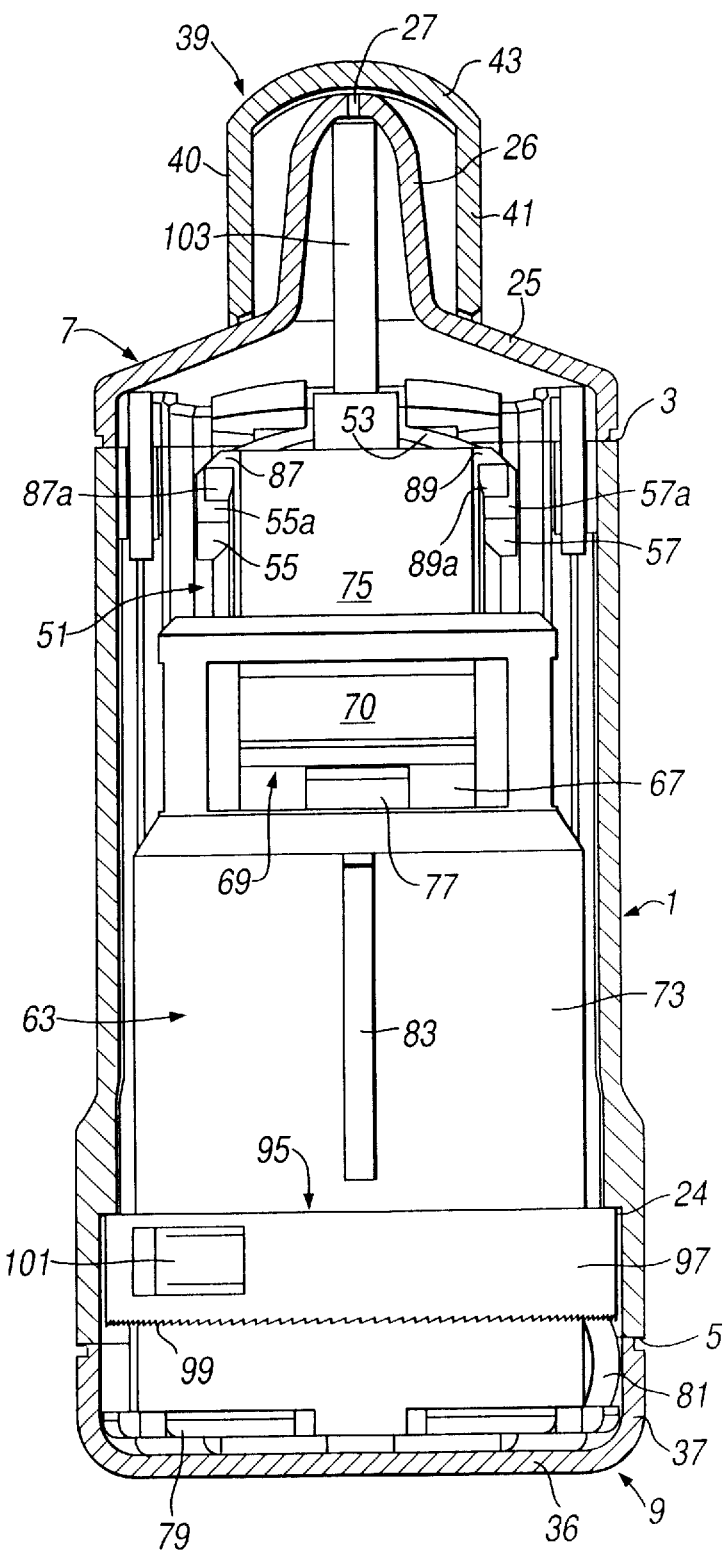
Figure 11:
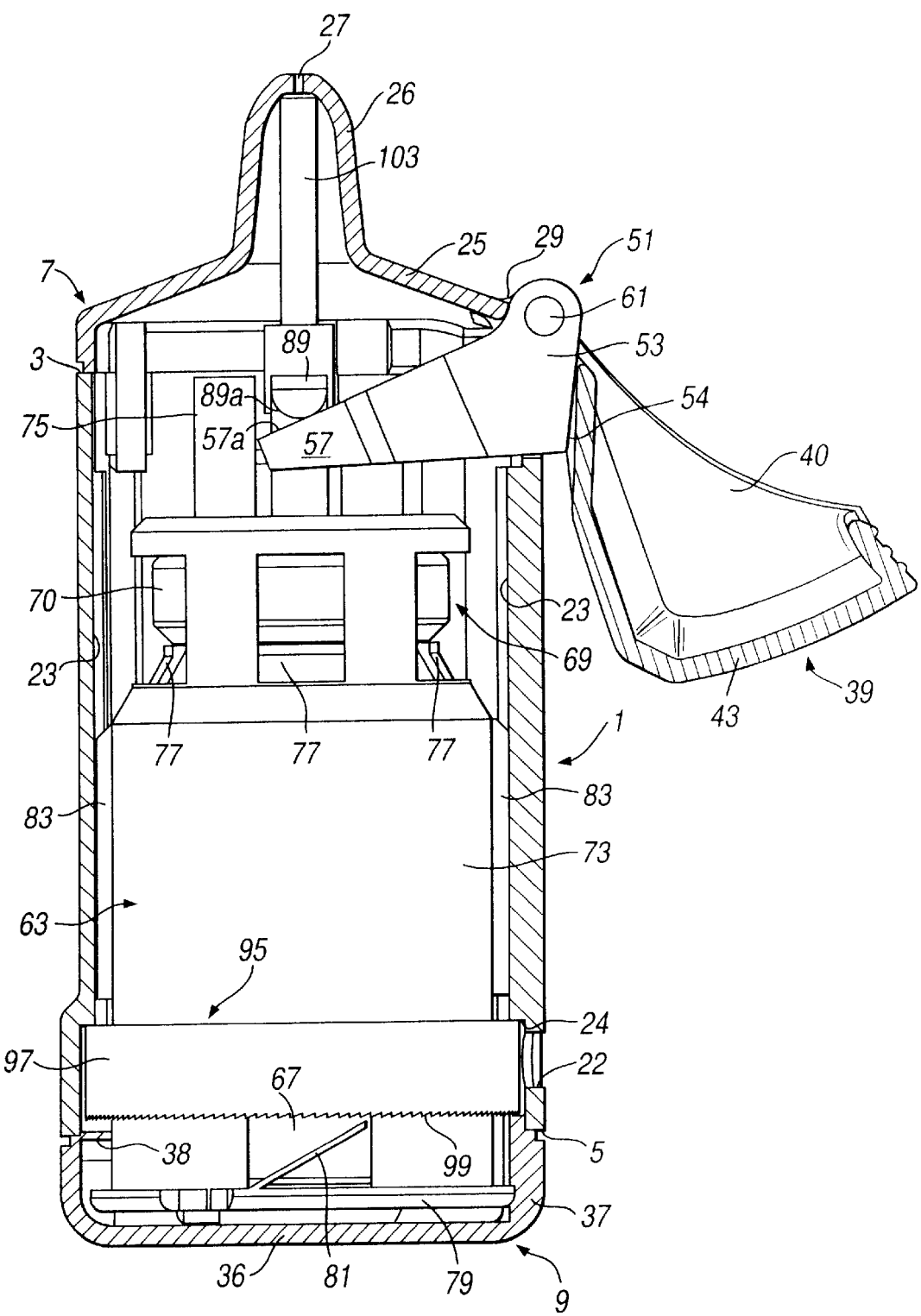
FIGS. 11 and 12 illustrate vertical sectional views (along sections I—I and II—II in FIGS. 3 and 4 respectively) of the delivery device in the open, but non-actuated configuration.
Figure 12:
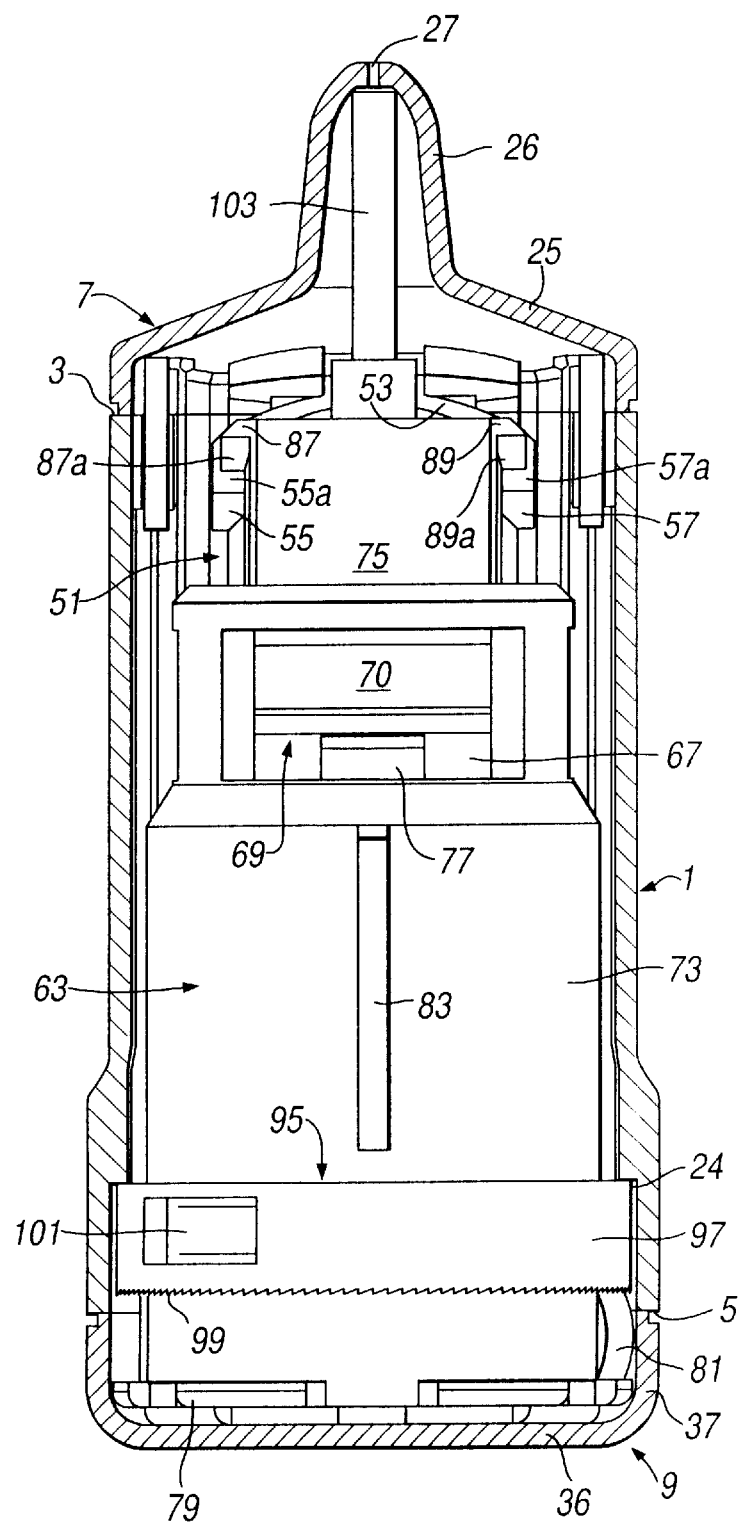
Figure 13:
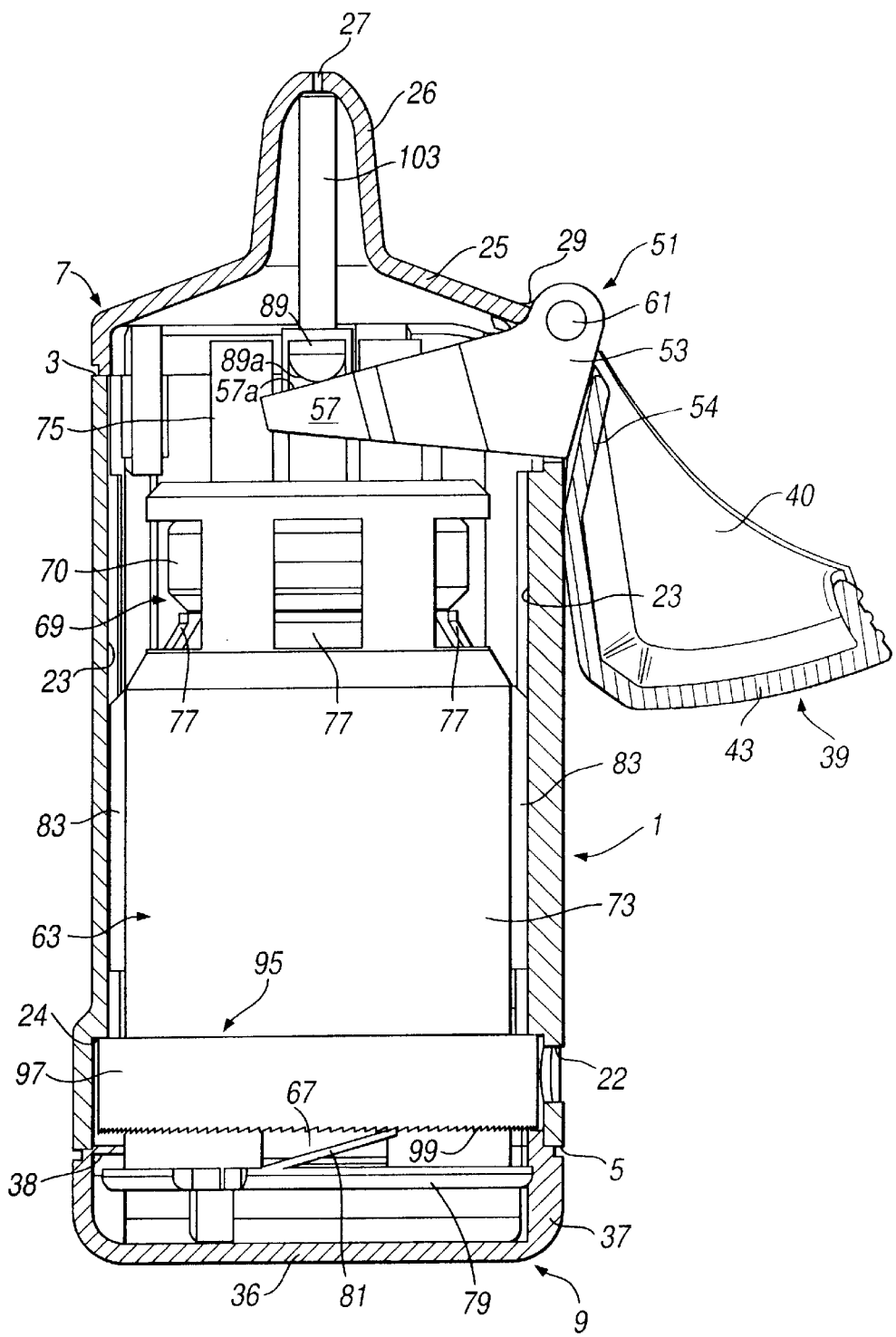
FIGS. 13 and 14 illustrate vertical sectional views (along sections I—I and II—II in FIGS. 3 and 4 respectively) of the delivery device in the open and actuated configuration.
Figure 14:
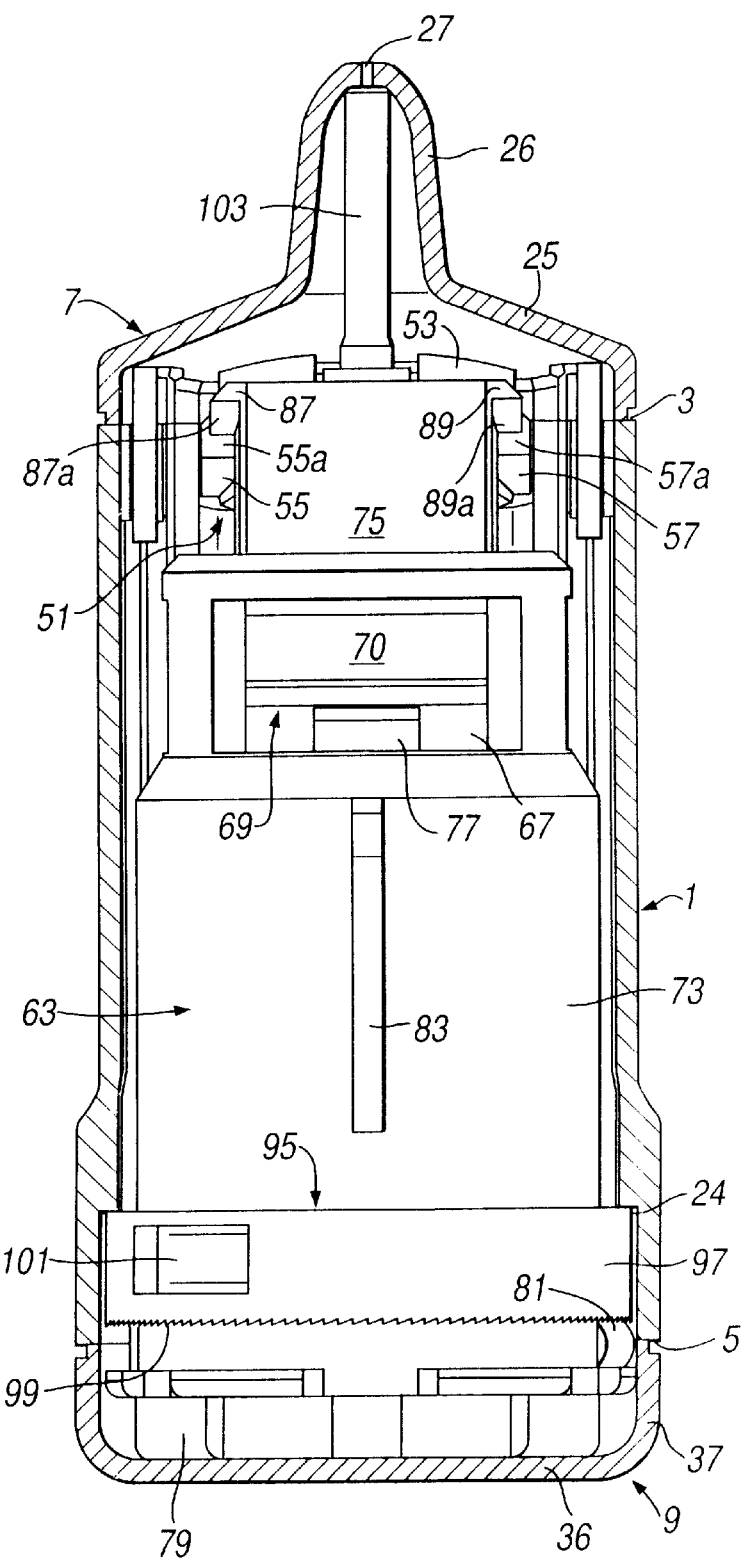

In use, a user takes the delivery device in one hand and lifts the cover member 39 so as to rotate the same from the closed position (as illustrated in FIGS. 9 and 10) to the open position (as illustrated in FIGS. 11 and 12) in which the tubular section 26 providing the nosepiece is exposed for insertion into a nasal cavity. In this open position, the part of the interconnecting member 43 of the cover member 39 which is adjacent the projections 45, 47 which define the hinge axis contacts the exposed bearing surface 54 on the body part 53 of the yoke member 51 and the delivery device is ready for use. The user then inserts the nosepiece provided by the tubular section 26 into a nasal cavity and actuates the delivery device by applying a force to the cover member 39 which now acts as a lever when rotated further in the same sense as in which the cover member 39 was opened. In applying a force to the cover member 39 further to rotate the same, the yoke member 51, through engagement between the part of the interconnecting member 43 of the cover member 39 adjacent the projections 45, 47 and the bearing surface 54 of the body part 53 thereof, is rotated such that the arms 55, 57 thereof are moved upwardly. This rotation, through engagement of the arms 55, 57 of the yoke member 51 and the bearing surfaces 87a, 89a on the projections 87, 89 on the second tubular section 75 of the carrier unit 63, causes the carrier unit 63 to be slid axially upwardly within the main body part 1. This sliding movement of the carrier unit 63, in which the liquid delivery unit 65 is mounted, causes the tubular delivery element 71 of the pump 69 of the liquid delivery unit 65 to be moved into the body 70 thereof and thereby force a volume of liquid through the spray orifice 27 and into the nasal cavity as a spray; the tubular delivery element 71 being of fixed position in relation to the main body part 1 in which the carrier unit 63 slides. With this actuation of the delivery device the ring element 97 of the dose indicator 95 is rotated by engagement of the distal end of the resilient element 81 on the carrier unit 63 against the driving surface 99a of one of the teeth 99 on the lower edge of the ring element 97. This advancement of the ring element 97 causes a lower number to be visible through the second lateral opening 22 in the main body part 1, which number is in this embodiment representative of the number of doses remaining. After actuation of the delivery device the user then releases the actuation force applied to the cover member 39 and the carrier unit 63 is forced to slide axially downwardly, through the force of an internal resilient element in the pump 69, within the main body part 1 such as to return to the original position. At the same time, the yoke member 51 is also rotated back to the original position through the engagement of the projections 87, 89 on the second tubular section 75 of the carrier unit 63 and the arms 57, 59 on the yoke member 51. Further, this sliding movement of the carrier unit 63 causes the resilient element 81 thereon to disengage from the driving surface 99a of the one tooth 99; back-rotation of the ring element 97 of the dose indicator 95 being prevented by the resilient element 38 on the second end body part 9 which continuously engages the lower edge of ring element 97 such that the distal end of the resilient element 38 is always located adjacent the driving surface 99a of one of the teeth 99. The user then returns the cover member 39 to the closed position such that the spray orifice 27 in the tubular section 26 providing the nosepiece is enclosed and the delivery device is ready for further use. This operation of the delivery device can be repeated until the delivery device has been actuated a predetermined number of times, at which point the ring element 97 of the dose indicator 95 will have been rotated through such an angle that the resilient element 101 thereon is axially aligned with the opening 85 in the first tubular section 73 of the carrier unit 63 and on further actuation of the delivery device the resilient element 101 will locate in the opening 85 and lock the carrier unit 63 in a fixed position, in this embodiment the actuated position, to prevent further use of the delivery device.

Finally, it will be understood that the present invention has been described in its preferred embodiment and can be modified in many different ways without departing from the scope of the invention as defined by the appended claims.

What is claimed is:

1. A single-handed manually-actuated delivery device for the delivery of a volume of liquid into a nasal cavity comprising:

a housing which includes a nosepiece having an outlet through which liquid is delivered to the nasal cavity;

and a cover member which is movably disposed relative to the housing between a first position in which the cover member at least partly covers the outlet and a second position in which the cover member acts as a lever which in use is acted upon by one hand of a user, characterized in that a force applied by the user to the lever to actuate the delivery device is substantially orthogonal to an axis defined by a path of the delivered liquid exiting the outlet.

2. The delivery device according to claim 1, wherein the cover member is, in the first position thereof, configured completely to cover the outlet.

3. The delivery device according to claim 1, wherein the cover member is rotatably mounted to the housing.

4. The delivery device according to claim 3, further comprising a liquid delivery assembly which includes a liquid delivery unit which is configured to be actuated to deliver a volume of liquid to the outlet on actuation of the delivery device.

5. The delivery device according to claim 4, wherein the liquid delivery unit comprises a container for containing liquid and a pump for delivering a volume of liquid from the container to the outlet.

6. The delivery device according to claim 5, wherein the pump comprises a body and a tubular element which is movable relative to the body and through which a volume of liquid is in use delivered on movement thereof relative to the body.

7. The delivery device according to claim 4, further comprising a coupling member which is movably disposed to the housing and configured to be engaged by the cover member in the second position thereof and cause actuation of the liquid delivery unit when the cover member is acted upon by the user.

8. The delivery device according to claim 7, wherein the liquid delivery assembly is movably disposed to the housing such as to cause actuation of the liquid delivery unit when moved between first and second positions and the coupling member is configured to move the liquid delivery assembly between the first and second positions when the cover member is acted upon by the user.

9. The delivery device according to claim 8, wherein the liquid delivery assembly includes at least one projection and the coupling member includes at least one arm which is configured in use to engage the at least one projection to move the liquid delivery assembly between the first and second positions.

10. The delivery device according to claim 9, wherein the liquid delivery assembly is slideably disposed to the housing.

11. The delivery device according to claim 7, wherein the coupling member is rotatably mounted to the housing.

12. The delivery device according to claim 11, wherein an axis of rotation of the cover member and the coupling member are parallel.

13. The delivery device according to claim 12, wherein the axis of rotation of the cover member and the coupling member are co-axial.

14. The delivery device according to claim 4, wherein the liquid delivery assembly further includes a carrier unit to which the liquid delivery unit is attached.

15. A delivery device, according to claim 4, wherein the liquid delivery device unit includes a component which is moved on actuation thereof; and an indicator is provided to indicate a number of actuations of the delivery unit, which indicator includes a rotatable member which is configured to be rotated by actuation of the delivery unit;

wherein the rotatable member includes a resiliently-biased element and the component includes a locking surface, which resiliently-biased element and locking surface are configured such that the component is locked in position so as to prevent further actuation of the delivery device once the delivery unit has been actuated a predeterminable number of times.

16. The delivery device according to claim 15, wherein the rotatable member is configured to be rotated on each actuation of the delivery unit.

17. The delivery device according to claim 15, wherein the component is configured so as to move substantially parallel to the axis of rotation of an rotatable member.

18. The delivery device according to claim 15, wherein the component is reciprocally movable.

19. The delivery device according to claim 15, wherein the locking surface is provided by an opening.

20. The delivery device according to claim 19, wherein the opening is a through opening.

21. The delivery device according to claim 15, wherein the rotatable-member is disposed about the component.

22. The delivery device according to claim 21, wherein the rotatable member is disposed about an outer surface of the component.

23. The delivery device according to claim 22, wherein the outer surface of the component is cylindrical and the rotatable member is circular.

24. An inhalation device incorporating the delivery device according to claim 15.

25. An inhalation device incorporating the delivery device according to claim 1.

* * * * *